United States Patent [19]

Brule et al.

[11] Patent Number: 4,816,398

[45] Date of Patent: * Mar. 28, 1989

[54] CASEIN PHOSPHOPEPTIDE COMPOSITION

[75] Inventors: Gérard Brule; Loïc Roger, both of Rennes; Jacques Fauquant, Monfort; Michel Piot, Rennes, all of France

[73] Assignee: Institut National de la Recherche Agronomique, Paris, France

[*] Notice: The portion of the term of this patent subsequent to Jan. 22, 2002 has been disclaimed.

[21] Appl. No.: 820,840

[22] Filed: Jan. 22, 1986

Related U.S. Application Data

[60] Continuation of Ser. No. 637,733, Aug. 6, 1984, abandoned, which is a continuation of Ser. No. 388,931, Jun. 16, 1982, Pat. No. 4,495,176, which is a division of Ser. No. 229,062, Jan. 28, 1981, Pat. No. 4,358,465.

[30] Foreign Application Priority Data

Feb. 1, 1980 [FR] France .................................. 80 02281

[51] Int. Cl.$^4$ ..................... C12P 21/06; C07K 1/00; A23J 3/02; A23C 23/00
[52] U.S. Cl. ..................................... 435/69; 424/127; 424/128; 426/42; 426/491; 435/272; 514/7; 530/352
[58] Field of Search ............... 426/34, 42, 657, 491; 435/69, 272; 424/127, 128, 131, 140, 145, 147, 177; 530/352; 514/7

[56] References Cited

U.S. PATENT DOCUMENTS

| | | | |
|---|---|---|---|
| 3,974,294 | 8/1976 | Schmille et al. | 426/657 X |
| 4,172,072 | 10/1979 | Ashmead | 260/113 X |
| 4,303,580 | 12/1981 | Hidalgo et al. | 260/113 |
| 4,358,465 | 11/1982 | Brule et al. | 426/42 |
| 4,361,587 | 11/1982 | Brule et al. | 426/42 |
| 4,495,176 | 1/1985 | Brule et al. | 426/42 X |

OTHER PUBLICATIONS

Mellander, O., Pediatric Clinic and the Institute of Medical Chemistry, University of Uppsala, Sweden, 1949, pp. 247–255.
West, D. W., Journal of Dairy Research, vol. 44, No. 2, 1977 (pp. 373–376).
Nykkanen, et al., J. Nutr., vol. 110, 1980 (pp. 2141–2148).
Brule, et al., J. Dairy Sci., vol. 62, 1979 (pp. 869–875).
Roozen et al., Enzyme Microb. Technol., vol. 1, 1979 (pp. 122–124).

*Primary Examiner*—David M. Naff
*Attorney, Agent, or Firm*—Oblon, Fisher, Spivak, McClelland & Maier

[57] ABSTRACT

A casein phosphopeptide composition is prepared containing less than 4% phenylalanine, tyrosine and tryptophan, greater than 8% and less than 20% serine, a ratio of $Ca+Mg+P/N_T$ greater than 0.2, wherein $N_T$ is the total nitrogen content times 6.38, and free amino acids of less than 3%. The composition is useful as an ailment for dietetic or therapeutic nutrition or as a medicament. Salts of the phosphopeptides may be formed from macroelements such as calcium and/or magnesium and/or from oligoelements such as iron, zinc and copper. The composition is produced by proteolytic enzyme hydrolysis of a casein-based material, and using ultrafiltration and aggregration with a bivalent cation salt to isolate the phosphopeptide composition.

11 Claims, 2 Drawing Sheets

CASEIN PHOSPHOPEPTIDE COMPOSITION

This application is a continuation of application Ser. No. 637,733, filed Aug. 6, 1984, now abandoned, which is a continuation of application Ser. No. 388,931, filed June 16, 1982, now U.S. Pat. No. 4,495,176, which is a division of application Ser. No. 229,062, filed Jan. 28, 1981, now U.S. Pat. No. 4,358,465.

The present invention relates to the field of processing casein-based materials. More particularly, it has for its object a method involving treatment of phosphocaseinates of monovalent cations or derivatives thereof. The invention also relates to the products obtained by such a method, especially fractions enriched in phosphopeptides and in non phosphorylated peptides, respectively. The invention further relates to the applications of the thus obtained products, particularly as alimentary products adapted to meet specific nutrition requirements as well as medicaments.

It is known that the caseins of dairy raw materials, and most particularly of milk, contain phosphoserines which impact to the peptides wherein they occur valuable physico-chemical, technological and physiological properties. Among others, information on milk proteins will be found in the book by Mc Kenzie H. A. (1971) entitled "Milk proteins", Vol. 1 and 2, Academic Press, New York.

Due to the recent advancement as regards both the apparatuses and the understanding of the observed phenomena, membrane ultrafiltration has found broad acceptance in the milk industry, for milk treatment (see, for example, Maubois J. L. Mocquot G. (1971—Préparation de fromages à partir de pré-fromages liquides obtenus par ultrafiltration du lait "Le Lait", fasicule 51 508, 495–533). As the milk flows across the ultrafiltration membrane, the water, soluble mineral salts, lactose, low molecular weight nitrogenous compounds (peptides, free amino-acids) and water-soluble vitamins will pass through the membrane as an ultrafiltrate or permeate, while the proteins and associated components (calcium, phosphorus), fat globules and lipophilous elements will be retained, their concentration increasing as the aqueous phase removal proceeds; these form the retentate or proteic concentrate. Obtainment of high purity proteic concentrates requires both an ultrafiltration step and a diafiltration step. In the diafiltration step, addition of water or aqueous solution containing salts is effected, in continuous or discontinuous manner, into the ultrafiltration retentate. Simultaneously or subsequently, an equivalent amount of permeate is removed. The result of such operation is to deplete the amount of filterable elements in the retentate. The advantage of the membrane ultrafiltration technique is to keep milk proteins in their native form.

The method of the invention takes advantage of membrane ultrafiltration to effect fractionating of the components of the casein-based raw materials, but by combining said ultrafiltration step with an enzymatic hydrolysis step.

A number of methods are known for the hydrolysis of proteins, e.g. milk proteins. In fact acid hydrolysis does allow obtainment of free amino-acids solutions, but will destroy some of the latter. Alcaline hydrolysis will preserve tryptophane, but cause an insolubilization which substantially reduces the nutritive value of the initial proteinic concentrates.

Enzymatic proteolysis has been known and used for quite a long while for analytic or nutritional purposes, the main object being to solubilize the proteins. Abundant reports will be found in literature on numerous alimentary uses of soybean protein hydrolyzates (see Arai S., Noguchi M., Kurosawa S., Kato H. and Fujimaki M. (1970) Applying proteolytic enzymes on soybean, 6-deodorization effect) of fish proteins: (see Hevia P., Whitaker J. R. and Olcott H. S. (1976)—Solubilization of a fish protein concentrate with proteolytic enzymes. J. Argric. Food Chem. Vol. 24 (2) 383–385) or of colza, by action of animal, microbial or vegetable proteases.

However, application of those techniques to milk proteins on a commercial scale is still quite limited.

Enzymatic proteolysis is free from the drawbacks of the chemical processes. Conditions of hydrolysis are moderate and thus preserve the nutritional value of the products.

Generally, hydrolysis leads to peptides having a pronounced bitter taste. This feature acts to limit the use of such hydrolyzates for human alimentation. The degree of bitterness of an hydrolyzate is mainly dependent on the nature of the proteic substrate and the enzyme specificity. To remove bitterness, it was suggested to use the action of exopeptidases. See for example Arai S., Yamashita M., Kato H., Fujimaki M. (1970)—Agric. Biol. Chem. 34, 729, as well as Clegg K. M., Smith G. and Walker A. L. (1974)—Production of an enzymatic hydrolyzate of casein of a kilogram scale. J. Food Technol. 9, 425–431. Moreover, it was proposed to modify the peptides by addition of glutamic acid before the plasteic reaction. It is also possible to proceed by removal of the hydrophobous amino-acids.

However, all these known techniques are unsatisfactory and unfit to meet the requirements of the invention. In fact, an extensive solubilization, caused by the use of exopeptidase, will increase the amount of free amino-acids and especially of arginine, lysine, tyrosine, valine, phenylalanine, methionine and leucine, and the net result thereof would be to burden the systems for free amino-acids transport at the intestinal barrier, thus causing a reduction in the nutritional efficiency of the hydrolyzates. On the other hand, the intrinsic quality of the hydrolyzates will be modified since the aminoacid equilibrium itself is changed, this requiring additional provision of free amino-acids.

From the technological standpoint, enzymatic hydrolysis is most usually effected with a discontinuous reactor system. The enzyme is added to the proteinic solution to be treated. After a more or less prolonged residence time, in conditions promoting enzymatic activity and substrate attack, the pH is modified and the enzyme is deactivated by a mild thermal treatment. Centrifugation may be effected to remove the undigested insoluble fraction. However, according to this technique of discontinuous enzymatic hydrolysis reaction, it is difficult to use a high enzyme to substrate ratio. Now, it is known, see Robins R. C. (1978)—Effect of ratio of enzymes to substrate on amino-acid patterns released from proteins in vitro. Internat. J. Vit. Nutr. Res. 48, 44–52, that the enzyme/substrate ratio has a critical influence on the nature of the free amino-acids and peptides released during proteolysis. With a discontinuous process, the enzymes must be destroyed at completion of hydrolysis, when provided in excess as would be compulsory with the aforesaid high ratios.

It was also proposed to use reactors with fixed enzymes. However, these are attended by substantial drawbacks from the practical standpoint. As a matter of fact, the optimum conditions for enzyme activity, especially pH conditions, are shifting, so that the reactor operation is not satisfactory at all times. Moreover, bacteriological problems occur and plugging of the fixation beds as well as protein adsorption onto the substrate. Moreover, the enzymatic reaction tends to get inhibited as time elapses, due to the formation of an enzyme-proteic fragment complex. Inhibition may also be caused by the substrate nature. It is moreover very difficult to use multi-enzyme systems because of the phenomena of enzyme competition with respect to the substrate and because enzyme stability will vary with time.

The invention takes advantage of means already known in some other applications and which consist in using enzymatic reactors provided with membranes. Reference may be made for example, to the article by Cheftel C. (1972)—Solubilisation enzymatique du concentreé protéique de poisson. Essai de recyclage des enzymes. Ann. Technol. Agric. 21, (3) 423–433 which describes a membrane-type reactor applied to proteolysis of fish proteic concentrates. The ultrafiltration membrane permits the enzyme to be kept in solution within the reactor, as well as the proteinic substrate. Only the hydrolysis products, i.e. the peptides, are removed as their formation proceeds. However, in practice, the use of such a reactor is not easy, as pointed out by Cheftel. The substrate should be completely solubilizable by the enzyme and the proteic solution has to be of irreproachable bacteriological quality.

As documents showing the state of the art, the following references may further be quoted:

French Pat. No. 77,24 069 (publication No. 2,399,213) describes treatment of an hydrolyzate by ultrafiltration, then electrodialysis. This document evidences the fact that it was known to ultrafiltrate a proteic hydrolyzate. The method described in this patent makes it possible to produce a pure soluton of natural amino-acids;

French Pat. No. 74,39 311 (publication No. 2,292,435) relates to the obtainment of calcium phosphocaseinate from a milk ultrafiltration retentate. The teaching of this patent has therefore for its object production of calcium phosphocaseinate. It does not relate to the treatment of monovalent cation phosphocaseinates or derivatives thereof;

The reference Chemical Abstracts, Vol. 87, No. 19, Nov. 7, 1977, page 265, abstract 148 285 p Columbus, Ohio (US) & J. Dairy Research, Vol. 44 No. 2 (1977), pages 373–376, D. W. West "A simple method for the isolation of a phosphopeptide from bovine $\alpha s_1$-casein", describes the obtainment of a phosphopeptide from caseinate. The method involves enzymatic hydrolysis by trypsine, and fractionating steps by gel filtration and chromatography, but it begins by a reaction with CNBr leading to quite specific products;

The reference Chemical Abstracts, Vol. 91, No. 21, Nov. 19, 1979, page 523, abstract 173 597 g Columbus, Ohio (US) & Enzyme Microb. Technol., Vol. 1, No. 2 (1979), pages 122–124, P. P. Roozen and al. "Enzymatic protein hydrolysis in a membrane reactor related to taste properties" describes hydrolysis in an enzymatic reactor, with a view to improve the taste of proteic hydrolyzates. This document thus evidences the fact that the enzymatic reactor is a known apparatus.

According to the invention, the method of treatment is applied to proteic solutions free of bivalent ions, such as calcium and magnesium. As a matter of fact, there is essentially used a casein-based raw material containing monovalent cation phosphocaseinates or derivatives thereof.

Broadly speaking, the method of the invention is characterized in that the above-defined raw material is subjected to enzymatic hydrolysis by means of at least one proteolytic enzyme capable of simulating the proteic digestion occurring in vivo in the human body; the thus obtained hydrolyzate is subjected to at least one ultrafiltration step on membranes which allow all the peptides in the hydrolyzate to pass in the permeate; the permeate is added with at least one bivalent cation salt capable of forming aggregates with the phosphorylated fraction of said peptides, this leading to a solution which essentially contains aggregates of phosphopeptides and non phosphorylated peptides; and separation is effected by at least one ultrafiltration step between the non phosphorylated peptides and the phosphopeptides, the latter having a larger particle size, by bringing the solution into contact with at least one membrane capable of retaining said phosphopeptides.

The casein-based raw materials liable to be treated by the method of the invention contain monovalent cation phosphocaseinates, such as sodium, potassium or ammonium phosphocaseinates. The treatment may also be applied to a raw material containing derivatives of said phosphocaseinates, especially paracasein. All such compounds are known to those skilled in the art and are obtainable by industrial means. For example, preparation of monovalent caseinates, such as sodium caseinate, first involves preparation of casein, starting e.g. from milk, by precipitation at the isoelectric point. After washing said casein, the casein precipitate is added with sodium hydroxide, potassium hydroxide, ammonium hydroxide or other basic compounds including monovalent ions and adapted to resolubilize the casein. There is finally obtained a proteic solution containing said monovalent cation caseinates, preferably sodium and potassium caseinates. Such substances can be directly used as a raw material for the method of the invention.

In an alternate embodiment, use may be made of derivatives of said caseinates, in particular under the form of paracasein. For this purpose, the solution of monovalent cation phosphocaseinates is previously treated by addition thereto of rennet, which causes an hydrolysis reaction. The hydrolysis product will contain paracaseinates, and the caseinomacropeptides (CMP). The paracasein is then subjected to precipitation by any known means, preferably by acidification to pH 4.6 with any organic or inorganic alimentary or medical acid, e.g. hydrochloric acid, phosphoric acid, sulphuric acid, acetic acid, lactic acid or other similar acids. In practice, hydrochloric acid is preferred. Then, the supernatant solution, containing the caseinomacropeptides, is separated from the precipitated paracasein. The latter is used in turn as a raw material for the method of the invention. In this modified embodiment, the solution obtained contains caseinomacropeptide which may constitute a valuable product. To purify and separate said product, said solution may be neutralized with a basic compound, such as sodium hydroxide. The CMP can be prepared under a concentrated form by ultrafiltrating the solution, after addition thereto of calcium chloride.

In a preferred form of the above described alternate embodiment, the sodium caseinate in water solution (3%) was hydrolyzed by rennet (20 ml/100 l). The paracasein was then precipitated by acidification (to pH 4.6) with HCl. The supernatant solution containing the caseinomacropeptide was thenafter neutralized (to pH 7.0) with sodium hydroxide, and concentrated by ultrafiltration after being added with 0.5 g of $CaCl_2$. Upwards of 1000 liters of 3% caseinate solution, this alternate embodiment allows obtention of about 30-40 liters of 3% caseinomacropeptide solution.

Irrespective of the raw material used in the method of the invention, the initial step consists in an enzymatic hydrolysis with at least one proteolytic enzyme capable of simulating the proteic digestion occuring in vivo in the human body. As previously mentioned, such an hydrolysis is effected to advantage in a device which combines an ultrafiltration equipment with an enzymatic reactor, this permitting continuous operation.

In such an embodiment, the enzymatic hydrolysis step is effected continuously by feeding the casein-based raw material to a reaction zone to bring it into intimate contact with the enzyme, the reaction product is withdrawn continuously and transferred from the reaction zone to an ultrafiltration zone, wherefrom there is withdrawn, also continuous by a permeate which forms the peptidic hydrolyzate.

During the enzymatic hydrolysis step, the pH should be adjusted in the range of 7 to 9. For this purpose, there is fed in continuous or discontinuous manner, into the reaction zone, a basic compound which may be sodium hydroxide or carbonate, potassium hydroxide or carbonate, ammonium hydroxide or a mixture thereof. The selection of a particular basic compound will depend on the intended purpose for the final product.

As an enzyme, use is made preferably of at least one proteolytic enzyme capable of simulating the proteinic digestion which occurs in vivo in the human body. Therefore, use may be made to advantage of pancreatin, which is a complex mixture containing trypsine, chymotrypsine and other secondary proteolytic enzymes. In practice, it may be resorted to a natural pancreatic extract commercially available and readily obtainable. However, if so required, use may also be made of enzymes formed by a synthetic mixture, e.g. of alpha-chymotrypsine and trypsine. Preferably, the synthetic mixture used has a composition approximating that of pancreatin, and therefore including the secondary enzymes contained in natural pancreatic extract. It was found according to the invention that at a pH ranging from 7 to 9, and preferably from 7 to 8.5, e.g. of 8, pancreatin and other similar enzymes meeting the requirements of the invention have maximum stability.

It is further advisable to comply with rather strict temperature conditions in the enzymatic hydrolysis zone. In fact, it was found that enzyme activity was more strongly influenced by the temperature than by the pH. In particular, tests have shown, according to the invention, that with trypsine, the maximum temperature during enzymatic hydrolysis should not be higher than 54° C., and that with chymotrypsine, said temperature should not be higher than 45° C. In practice, when use is made of pancreatin, a compromise will be made taking into account both the optimum conditions for intestinal proteolysis in vivo (temperature of the order of 37° C.) and the fact that higher temperatures are less favorable to germ growth and allow for higher ultrafiltration outputs. In general, the selected temperatures are of the order of 37° to 40° C., and most preferably still close to 37° C.

Obviously, the reaction parameters, viz. the pH and the enzymatic hydrolysis temperature, are interrelated. Thus, it will fall to those skilled in the art to select the most favourable conditions in each particular case.

To effect optimum enzymatic hydrolysis, it is also advisable to select carefully the ultrafiltration membrane to be used in conjunction with the enzymatic reactor. The membranes used may be of any organic or inorganic type. A membrane structure which afforded good results is that of modules with hollow fibers. As a guidance, use may be made of the membranes of Société Amicon available under the trade name H10P5 (cut-off threshold 5000) and H10P10 (cut-off threshold 10,000) as well as membranes of Societé ROMICON available under the trade name PM2 (cut-off threshold 2000) or PM50 (cut off threshold 50,000). The only requirement to be met is that, in operation, the membrane should retain efficiently the enzyme, while having satisfactory performances, especially as regards its life time.

The method of the invention may be carried out in two separate stages: a first stage consisting in the enzymatic hydrolysis step, and a second stage consisting in the ultrafiltration step associated with said hydrolysis step. The equipments for carrying out each of these steps can be separate or integral. However, as an alternate embodiment, the method may also be performed continuously, both aforesaid stages being effected in a single apparatus. During the initial operating period, e.g. for about one hour, the permeate (liquid flowing through the membrane) is recycled to the hydrolysis zone for the obtention of the desired degree of hydrolysis of the casein-based material. After hydrolysis, the reactor is fed with the casein-based raw material to be treated at a flow-rate identical with that of the permeate.

Thus, a preferred embodiment of the invention consists in combining and carrying out continuously the enzymatic hydrolysis step and the membrane ultrafiltration step, whereby all the peptides in the hydrolyzate can be recovered in the hydrolyzate. The ultrafiltration membrane used in conjunction with the enzymatic hydrolysis step should have such characteristics as to allow free passage of all the peptides in the hydrolyzate. Membranes having a cut-off of 50,000 or more proved to be suitable.

According to an essential feature of the invention, the permeate had added thereto at least one bivalent cation salt able to form aggregates with the phosphorylated fraction of the peptides. Indeed, it was found that by complexing the bivalent cations, inter-aggregation of the phosphopeptides is facilitated, whereby the latter can be separated from the non phosphorylated peptides. Separation between the phosphopeptides and the non phosphorylated peptides obtained upon enzymatic hydrolysis is based on the ability of phosphoserines to complex alkaline-earth ions, particularly calcium and magnesium ions. When, as is the case for the method of the invention, hydrolysis is effected on proteic solutions free of calcium and/or magnesium, it is important to add to the peptidic solutions obtained upon hydrolysis the involved bivalent cations, which exert the complexing function.

In practice, it is preferred to use, as complexing bivalent cations, calcium cations, for example brought in by calcium chloride. The amount of agent for complexing the bivalent cation-based peptides which, according to the invention, should be added to the peptidic solution is not critical. Practically, calcium chloride amounts of the order of 0.5% by weight, as related to the peptide solution, were deemed suitable. Obviously, it rests with those skilled in the art to select the bivalent compounds and amount thereof to be used, also taking into account the features of the subsequent stage of separation between the phosphopeptide aggregates and non phosphorylated peptides, said separation being effected, according to the invention, by an ultrafiltration step. In other words, due attention should also be paid especially to the cut off threshold of the ultrafiltration membrane, so as to avoid passage of the phosphopeptidic aggregate through this membrane.

According to an embodiment which afforded good results, there is used in association with the complexing agent a mineral phosphate, such as sodium acid phosphate $PO_4HNa_2$. The presence of such a phosphate compound may enhance the complexing action and formation of large phosphopeptidic aggregates. However, in some cases and especially when it is desired to obtain, at the end of the treatment, phosphopeptides fractions without exaggerated mineral phosphate enrichment, then the amount of phosphate added may be reduced, or even completely suppressed, provided that there is used at the final stage of the process a membrane capable of retaining the phosphopeptides and with a cut-off threshold ranging preferably between 2000 and 50,000, and more preferably between 2000 and 10,000.

As previously mentioned, each of the above ultrafiltration steps may be followed by a diafiltration step during which there is added, continuously or discontinuously, a liquid such as water or aqueous salt-containing solution, with a view to further purify the ultrafiltration products. In the method of the invention, water proved to be suitable for diafiltration.

As a result of the ultrafiltration and diafiltration steps which follow the enzymatic hydrolysis step, there is obtained, on the one hand, a peptidic solution which is subjected to further treatment by the method of the invention, and on the other hand a fraction (retentate) which consists of proteic residue and residual enzymes. As a result of the ultrafiltration and diafiltration steps effected at the final stage of the method of the invention, there is obtained on the one hand, as a permeate, non phosphorylated peptides, and on the other hand, as a retentate, phosphopeptides.

In a preferred embodiment, preparation of the peptidic fractions was effected starting from a 6% sodium caseinate solution. Hydrolysis in the enzymatic reactor was done with pancreatin in an amount of 4 g/l at pH 8 and at 37° C. The reactor content was then diafiltrated with water. The peptide solution was thereafter acidified to pH 6.2, aggregation being caused by addition of $CaCl_2$ (0.5%) and $PO_4HNa_2$ (0.2%). The peptide solution then undergone ultrafiltration and diafiltration. Starting from 1000 liters of 6% sodium caseinate, there may be obtained 900 liters of non phosphorylated peptidic solution (45 g/liter) and 100-120 liters of phosphopeptide solution (80 g/liter).

The phosphopeptides thus obtained at the final stage of the method of the invention constitute the most interesting valuable product. Indeed, the latter has a high phosphoserine content and contains low amounts of aromatic amino-acids (phenylalanine, tyrosine, tryptophane).

The thus obtained fraction, rich in phosphopeptides, may therefore be characterized both by its particular composition in amino-acids and by a high content of mineral matter (ashes) with respect to the total nitrogen, as the phosphopeptidic fraction acted to complexe the added salts.

Table I hereunder shows the main characteristics of the products of the invention, those of the monovalent caseinate being set forth in the first column, as a reference.

TABLE I

| | K or Na caseinate | Non phosphorylated peptides | Phosphopeptides |
|---|---|---|---|
| Total amount of aromatic amino-acids (Tyr, Phe, Trp) | 12% | >12% | <4% |
| Serines | 4,9% | <4% | <20% >8% |
| $\dfrac{Ca + Mg + P}{N_T(1)}$ | <0,01 | <0,02 | >0,2 |
| Free amino-acids | — | <10% | <3% |

(1) $N_T$ = total nitrogen × 6.38

The phosphopeptides obtained by the method of the invention are suitable for numerous applications in the alimentation field.

The products of the invention are useful for alimentation, in particular human alimentation, and for therapeutic nutrition. It is known indeed that, in human milk, the so-called organic phosphorus, i.e. bound to the proteins and bound to the lipids, is comparatively more abundant than in other milks, especially cow's milk. Thus the ratio $$\frac{\text{organic phosphorus}}{\text{total phosphorus}}$$

is of about 0.83 in human milk as against 0.34 in cow's milk.

More precisely, the ratio of organic phosphorus bound to the nitrogen versus inorganic phosphorus is about 0.70 in human milk against 0.36 in cow's milk.

Therefore, the products of the invention will found applications in the field of so-called milk maternisation.

But, in general, it is admitted that the main good property of woman's milk proteins is to ensure a remarkable nitrogen anabolism, together with renal osmotic load and a $H^+$ ion load of particularly low values.

Now, this conjunction of a very high nitrogen anabolism with low renal osmotic load and $H^+$ ion-load is particularly sought in the fields of reanimation and therapeutic nutrition, where high anabolism requirements and functional renal deficiency are quite often coexistent.

The products of the invention are suitable to meet those requirements. For certain applications, the products of the invention contain an insufficient amount of some essential amino-acids (phenylalanine, tryrosine, tryptophane, cystine). They may then be associated to advantage with other proteins or peptides or either alpha-keto-acid or alpha (OH) acid homologues of essential amino-acids, for restoring of a good amino-acid equilibrium leading to optimal biological value.

It will also be noted that such products (phosphopeptides) have a high affinity for macroelements (calcium, magnesium) and for oligoelements as, particularly, iron, zinc, copper, chrome, nickel, cobalt, manganese and selenium.

The phosphopeptides according to the invention can advantageously be converted into salts of said elements by usual means. Thus, to obtain such an organophosphorated salt, it may be used, as a diafiltration solution for purifying the phosphopeptides, a solution of a salt containing the element to be introduced, e.g. a solution of iron chloride in the case of iron. These organophosphorated salts are highly soluble and they may advantageously be used as carriers for the particular elements.

The products of the invention meet the nutritional requirements of patients suffering from pancreatic deficiency, metabolic diseases, nutritional deficiency or distress, which may be or not associated with a functional or organic renal deficiency, in particular when they are associated with peptides, essential amino-acids or essential amino-acid homologues.

The invention therefore finds a direct application in dietetic aliments or therapeutic nutriments which are perfectly assimilable by the human body.

Irrespective of the source of proteins, peptides or amino-acids used, these phosphopeptides permit to regulate, in the most desirable manner, the amount of organic phosphorus bound to nitrogen in the formulation to be created.

As previously mentioned, the phosphopeptides according to the invention and their derivatives, notably the organophosphorated salts which they form and the mineralmacroelements, such as calcium and/or magnesium, and/or with oligoelements (Fe, Zn, Cu, Cr, Ni, Co, Mn, Se for instance) find an interesting application in the dietetic.

The invention concerns therefore dietetic compositions containing an efficient quantity of at least one such phosphopeptide or derivatives of phosphopeptide in association with a carrier acceptable form the nutritional point of view. Such as efficient quantity may vary in wide limits according to the effect seeked. For information purpose, a quantity in weight of 10% with respect to the total of the composition is suitable in the usual cases.

The products of the invention can also be applied as such, as medicaments for man and animal.

The medicaments concerned are appropriated to alleviate all diseases involving a lack of organic phosphorus and of certain mineral elements. For illustration purpose and not at all limitative, some specific examples of such application are hereafter given.

The mineral derivatives of phosphopeptides according to the invention, consisting of their calcium salts, constitute a protidic mineral supplement rich in organic phosphorus and in calcium. They find an application as medicaments, for instance in the following cases:
  recalcification of bones after fracture,
  osteoporosis treatment
  calcic addition during treatment of rickets.

The derivatives of phosphopeptides according to the invention, consisting in their manesium salts, constitute a mineralo-protidic supplement rich in organic phosphorus and in magnesium. They find an application as medicaments to remedy to all the forms of magnesic deficit, more particularly to the adult, for instance in the following cases:
  needs in Mg greatly increased by the stress
  bad use of Mg food by the old people
  increase of Mg-needs to the pregnant woman.

Medicaments containing derivatives of phosphopeptides consistigng in mixt calcium and magnesium salts, are used in the same way as minerolo-protidic supplement. It goes without saying that similar applications can be foreseen of varied phosphopeptides salts according to the invention, although, in practice, calcium and/or magnesium salts are preferred.

It is to be noted that the phosphopeptides, such as they are obtained according to the process of the invention are under the form of their salts of bivalent cations, particularly salts of calcium and/or magnesium. If necessary, such salts can be converted into neutral phosphopeptides by lowering the pH of the medium for example to 4.6 about, but in practice, this procedure is not compulsory, because the phosphopeptide salts are perfectly suitable to be used as such. Thus in the condition of use, and more particularly when the phosphopeptides are included in dietetic or pharmaceutical compositions, they are found under the form of salts, for instance of calcium and/or magnesium.

The macroelements (preferably calcium and/or magnesium) can be replaced, at least partially, by oligoelements.

The derivatives of phosphopeptides according to the invention which contain oligoelements find an application corresponding to that of particular oligoelements.

The general indications of medicaments containing phosphopeptides and oligoelements derivatives are among others the digestive bad absorptions inducing lack of oligoelements (Fe, Zn, Cu, Cr, Ni, Mn, Se). Said digestive bad adsorptions appear more particularly during inflamatory ileitis, in the case of resect bowels, celiac diseases and radic bowels. As examples, the lack of zinc can cause acrodermatitis enteropathica, diarrhoeas, an increased sensitiveness to infections, hypogonadism. Lacks of iron can entail sideropenic anemia.

The medicaments according to the invention are preferred for the treatment of lack of zinc, copper, chromium and iron.

The invention also concerns pharmaceutical compositions containing a product of the invention in admixture with the usal excipients. Taking into account the physical form of the new product (soluble powder in aqueous medium), the form of presentation does not raise any difficulty. The new products can be ingested or given as such, especially by enteral tract, for instance mixed with usual food. They can also be presented under the form of compositions with usual excipients for instance suitable by oral administration. Appropriated compositions according to the invention can thus be presented under the form of tablets or capsules, with known excipients such as talcum, magnesium stearate, finely divided silica, and any other similar carrier known by the man skilled in the art.

As example, it has been indicated hereunder a particular case illustrating the preparation of pharmaceutical compositions for administration by oral route. Tablets have been prepared in the usual manner starting with the following formulation:
  phosphopeptide (or phosphopeptide salts) according to the invention: 200 mg
  excipient QS for a table terminated at: 300 mg The excipient used can be talcum, magnesium stearate or the silica available on the market under the denomination "aerosil".

Capsules dosed at 100 mg of phosphopeptide (or salt) according to the invention and containing an usual excipient QS for a capsule terminated at 200 mg have been prepared in the same manner.

The invention will now be illustrated by no way of limitation by the following description and examples given hereunder.

The description will be made with reference to the appended drawings, wherein.

Figure 1:
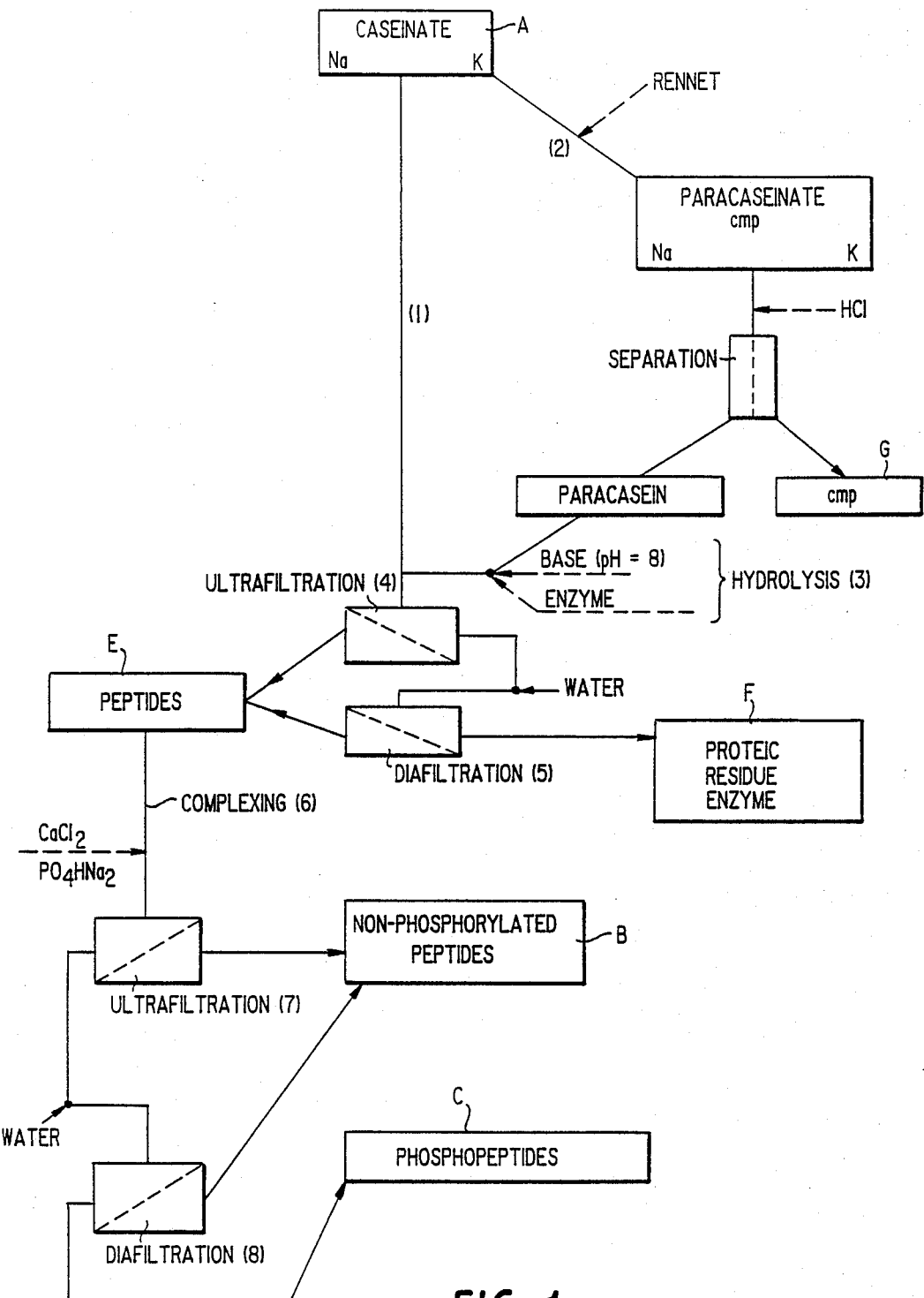
FIG. 1 is a flow-sheet illustrating the method of the invention.

As shown in FIG. 1, the monovalent (sodium or potassium) caseinate-basedraw material A can be subjected either directly to the process (reference 1) or to a previous treatment through the alternative path 2. According to this alternative embodiment, the raw material is hydrolyzed with rennet to form a solution containing the corresponding (sodium-or potassium-)paracaseinate and the caseinomacropeptide. The paracasein is precipitated by acidification (HCl). Then, separation is effected between the precipitated paracasein and caseinomacropeptide. The latter (CMP) constitutes a by-product G of the method which, while those steps are not shown, may be neutralized, e.g. by sodium hydroxide, and thereafter concentrated by ultrafiltration after beind added with calcium chloride.

Therefore, the raw material for the method is either caseinate A or its derivative, viz. paracasein.

The initial stage of the method is an hydrolysis (reference 3) in an enzymatic reactor. In the drawing, there is shown addition of a base adapted to raise the pH to 8, so that the hydrolysis will proceed satisfactorily with a proteolytic enzyme such as pancreatin. The hydrolysis product is thereafter subjected to an ultrafiltration (4), then to a diafiltration (5) with water. There is obtained both a peptidic fraction E, and a residual fraction F containing the residual proteins and enzyme. It is the peptidic fraction E which undergoes further processing in the method. The subsequent stage is a complexing step (reference 6) during which fraction E is added with calcium chloride and possibly with a phosphate ($PO_4HNa_2$). Upon complexing or aggregation of the peptides, the product is subjected to an ultrafiltration 7, then a diafiltration 8 with water. There is thus finally obtained a fraction B (permeate) which is enriched in non phosphorylated peptides, and a fraction C which is enriched in phosphopeptides.

Figure 2:
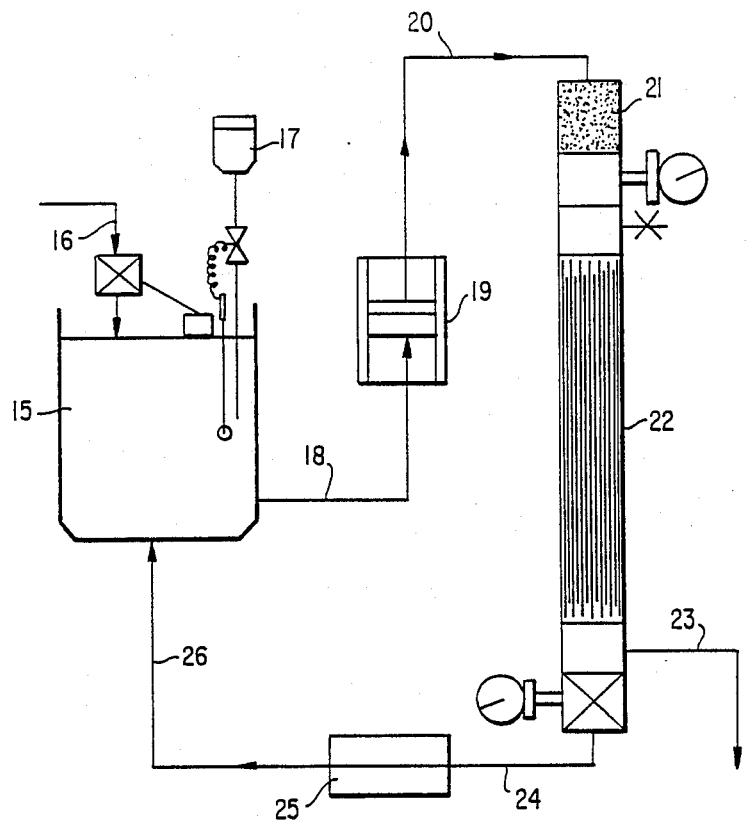
FIG. 2 is a diagram of an enzymatic reactor suitable for use in the method of the invention.

FIG. 2 shows a membrane-type enzymatic reactor which may used in the method of the invention.

Said reactor includes first a reaction tank generally designated by reference 15. Continuous feeding of phosphoscaseinates occurs through duct 16. A device 17 serves both to measure the pH and to keep it constant in the reaction tank by neutralizing the $H^+$ ions released when the peptidic bonds are broken. Said device was a a Mettler pH-stat comprising a a potential amplifier, and equivalence point presetting switch and automatic burette for feeding the reactive, the latter being a basic compound such as mentioned above. No excessive electrode fouling was noted. The hydrolysis product withdrawn from the reaction tank through duct 18 is conveyed by an automatic membrane-type pump 19. A practical example is the pump of Amicon lp 20 A model, with an output of 720 l/h at about 25 psi. At the outlet of the pump, the product flows through a duct 20 and is fed onto a pre-filter 21 having a pore size of 150 microns. Reference 22 designates the ultrafiltration module. In a specific example, the system used was Amicon DC 10 S model having ultrafiltration cartridges of the hollow fiber type. The permeate was recovered through a duct 23 and formed the desired peptidic hydrolyzate. The retentate was withdrawn from module 22 through duct 24, then fed to an exchanger 25 and conveyed through duct 26 to be recycled into reaction tank 15.

| Type | cut-off | surface area | Manufacturer |
|---|---|---|---|
| H 10 P 5 | 5000 | 0,9 m² | AMICON |
| H 10 P 10 | 10,000 | | |
| PM 2 | 2000 | 1,4 m² | ROMICON |
| PM 50 | 50,000 | | |

EXAMPLE 1

In this example, sodium caseinate is used as a raw material.

The caseinomacropeptide and peptidic fractions according to the process shown in FIG. 1 were prepared in two stages:

(1) Sodium caseinate in solution in water (3%) was hydrolyzed in a tank with rennet (20 ml/100 liters-BOLL rennet, 1/10,000) at 37° C. at pH 6.8 during 50 minutes. The paracasein was then precipitated by acidification to pH 4.6 with hydrochloric acid 4N; 440 ml of acid were necessary for 100 l of serum.

After settling, the supernatant containing the CMP was filtered on a gauze, then centrifuged (1000 g during 8 min.) after pH re-adjustment to 6.6 with potassium hydroxide 2N. This solution was thereafter concentrated by ultrafiltration on a membrane, being added with $CaCl_2$ (0.5 g/l). The apparatus used was an Amicon module of type DC 10 equipped with Romicon membranes of Hollow Fiber type XM 50 having a surface area of 1.4 m².

The chemical analysis of the various products obtained in this production run are set forth in tables II and III.

TABLE III

| Composition in amino-acids (g of amino-acid for 100 g) | | |
|---|---|---|
| Asp 6.9 | Gly 1.4 | Ile 10.3 |
| Thr 9.6 | Ala 6.1 | Leu 3.5 |
| Ser 3.1 | Cyst ε | Tyr ε |
| Glu 23.2 | Val 8.7 | Phe 1.7 |
| Pro 12.7 | Met 1.5 | Lys 6.6 |
| | | His 0.6 |
| | | Arg 0.9 |

(2) The sodium caseinate in solution in water (6.2%) was hydrolyzed in a membrane enzymatic reactor identical with that shown in FIG. 2. The membranes used were of the Hollow Fiber type XM 50, having a surface area of 4.9 m². The enzyme (Sigma pancreatin of bovin origin having an activity 4 NF) was added at a concentration of 4 g/liter. The reactor pH was kept at 8 by addition of potassium hydroxide 2N. Hydrolysis proceeded at 37°-40° C. Before being collected, the permeate was recycled in the tank during one hour. The thus obtained permeate contained the phosphopeptides and non phosphorylated peptides. The permeate was acidified to pH 6.4, then phosphopeptide aggregation was caused by addition of $CaCl_2$ (0.6% and of $PO_4HNa_2$ (0.1%). Thereafter, fractionating of the two groups of peptides was effected by ultrafiltration and diafiltration with water so as to remove the whole non phosphorylated peptide fraction. The concentration and diafiltration steps were carried out on membranes of XM 50 type at pH 6.5 and at temperatures of 8° C. The diafiltrated concentrate obtained corresponded to the phosphopeptidic fraction.

TABLE II

|  | Dry matter | $N_T \times 6.38$ | NPN* TCA 6% | NPN* TCA 12% |
|---|---|---|---|---|
| Starting caseinate (A) | 31.2 | 27.1 | — | — |
| Caseinate after rennet action | — | — | 182.5 | 95.4 |
| Renneted lactoserum after centrifuging, pH re-adjustment and CaCl$_2$ addition | 3.45 | 1.88 | 166.8 | 105.8 |
| Lactoserum concentrated by ultrafiltration or CMP(G) | 31.3 | 30.1 | 2649 | 1191 |
| Ultrafiltration permeate | 2.07 | 0.3% | — | — |

Chemical composition of the products as expressed in g/kg, except for non proteic nitrogen (NPN) expressed in ppm of nitrogen The analysis of the various products are shown in tables IV and V hereunder:

TABLE IV

Chemical composition of the products obtained

|  |  | Dry matter g/kg | $N_T \times 6.38$ g/kg | Ca g/kg | Ashes g/kg |
|---|---|---|---|---|---|
| (A) | Starting caseinate | 62.3 | 54.2 | — | — |
| (E) | Total peptides | 62.3 | 45.9 | — | — |
| (B) | Non phosphorylated peptides | 53.7 | 47.3 | — | — |
| (C) | Phosphopeptides | 15.0 | 7.90 | 2.35 | 6.3 |

TABLE V

Compositions of the amino-acids in the phosphopeptide (g of amino-acid per 100 g)

| Asp 5.6 | Cys ε |
|---|---|
| Thr 3.3 | Met 0.45 |
| Ser 18.5 | Ile 9.5 |
| Pro 4.7 | Leu 2.9 |
| Clu 36.8 | Tyr ε |
| Cly 1.7 | Phe ε |
| Ala 2.8 | Lys 0.9 |
| Val 8.7 | His 0.5 |
|  | Arg 0.3 |

The Illustrative examples relating to the applications of the products of the invention will be given hereunder, while implying no limitation.

EXAMPLE 2

This example relates to a reanimation product intended for: enteral administration to patients requiring a proteic input of about 7 to 15% of the total calorific input (TCI), for instance in the following ailments mucoviscidose or cystic pancreas fibrosis, renal deficiency, patients having an infectious or inflammatory disease of the intestinal membrane, nutrition distress requiring intense anabolism with reduced renal osmotic load and H+ ion load. These proteins are preferably brought into a pre-digested state.

Example of centesimal formula according to the invention

| Phosphopeptides from | 4 to 8% | |
| Lactoserum peptides | 60% | |
| Casein peptides from | 32 to 36% | 2.50 g |
| CMP from | 0 to 4% | |
| Lipids: | | |
| mixture in equal parts of: | | |
| butter oil | 0.5 g | |
| mean chain triglyceride (MCT) | 0.5 g | |
| maize oil | 0.5 g | 4.10 g |
| sunflower oil | 0.5 g | |
| glycerol monostearate | 2.1 g | |
| glucids: | | |
| glucose polymers | 10 g | |
| glucose | 1.5 g | 13.00 g |
| galactose | 1.5 g | |
| vitamins: | | |
| A, D, E, B$_1$, B$_2$, PP, B$_5$, B$_6$, B$_{12}$, folic acid, Biotine, C vit. | | according to FAO/MW0 recommendations |
| mineral elements: | | |
| (calcium, sodium, potassium, magnesium, phosphorus, zinc, iron, copper, manganese, chlorine, iodine) | | 0.455 g |
| distilled water | | as required for 100 g |

EXAMPLE 3

This example relates to a reanimation product for enteral administration to patients requiring a proteic input of about 12-25% of the Total Calorific Input, under the form of proteins. Such alimentation is suitable for any situation necessitating substantial nitrogen anabolism and an oversupply of organic P—.

EXAMPLE OF CENTESIMAL FORMULA

| mixture of small peptides according to the invention. | | |
|---|---|---|
| phosphopeptides from | 8 to 28% | |
| lactoserum peptides from | 22 to 60% | 3 to 6.25 g |
| casein peptides from | 12 to 70% | |
| lipids: | | |
| T.C.M. | 2.30 g | |
| Oil very rich in essential fatty acids | 0.50 g | 2.90 |
| Emulsifier | 0.10 g | |
| glucids: | | |
| Small glucose polymers from | 8.25 to 10.5 g | |
| Glucose from | 2 to 2.5 g | 12.25 to 15.5 g |
| Galactose from | 2 to 2.5 g | |
| vitamins: | | |
| A, D, E, B$_1$, B$_2$, PP, B$_5$, B$_6$, B$_{12}$, folic acid, Biotine, Vit. C | | according to FAO/MW0 recommendations |
| mineral elements: | | |
| (calcium, sodium, potassium, magnesium, phosphorus, zinc, iron, copper, manganese, | | 0.455 g |

EXAMPLE 4

This example relates to a reanimation product for enteral administration to patients requiring a proteic input of the order of 7–12% of the T.C.I., in particular in the following ailments: micoviscidose or cystic pancreas fibrosis, renal deficiency, patients having an infectious or inflammatory disease of the intestinal membrane, nutrition distress requiring intense anabolism with a reduced renal osmotic overload and a reduced H+ ion load. These proteins are preferably brought into a pre-digerted form Example of centisimal formula

| | | |
|---|---|---|
| mixture of small peptides according to the invention: | | |
| phosphopeptides | 4% | |
| casein peptides | 36% | |
| lactoserum peptides | 40% | 2.50 g |
| CMP | 20% | |
| lipids: mixture in equal parts of: | | |
| butter oil | 0.5 g | |
| MCT | 0.5 g | |
| maize oil | 0.5 g | 4.10 g |
| sunflower oil | 0.5 g | |
| glycerol monostearate | 2.1 g | |
| glucids: | | |
| glucose polymers | 10 g | |
| glucose | 1.5 g | 13.0 g |
| galactose | 1.5 g | |
| vitamins: | | |
| A, D, E, $B_1$, $B_2$, PP, $B_5$, $B_6$, $B_{12}$, folic acid, Biotine, C vit. | | according to FAO/MW0 recommendations |
| mineral elements: | | |
| (calcium, sodium, potassium, magnesium, phosphorus, zinc, iron, copper, manganese, chlorine, iodine) | | 0.455 g |
| distilled water | | as required for 100 g |

The peptide mixture containing the phosphopeptides according to the invention may include to advantage the peptides obtained according to the method described in French Patent Application filed on June 26, 1979 under No. 79 16 483 in the name of Institut National DE LA Recherche Agronominque for "Hydrolysat enzymatique total de protéines de lactosérum, obtention et applications". It will be recalled that such a peptidic hydrolyzate contains substantially no residual proteins and that 50% of the peptides contain 2 to 5 aminoacids. More particularly, the hydrolyzate contains 70 to 90% of the nitrogen present under the form of peptides having a number of amino-acids lower than 10. Under a specific form, the hydrolyzate corresponds to the following aminogram.

| Aminogram: | |
|---|---|
| Ile 6.0 | Arg 2.7 |
| Leu 9.9 | His 1.7 |
| Lys 9.2 | Ala 4.9 |
| Cys 1.8 | Asp 9.5 |
| Phe 3.2 | Clu 7.6 |
| Thr 6.7 | Cly 1.7 |
| Tyr 3.6 | Pro 6.2 |
| Trp 2.0 | Ser 5,5 |
| Val 5.5 | Met 2.0 |

The process for obtaining such an hydrolyzate consists in effecting first ultrafiltration of the lactoserum, then enzymatic hydrolysis thereof, and is more particularly characterized in that the ultrafiltration retentate is contacted with a proteolytic enzyme able to reproduce the proteic digestion occurring in vivo in the human body, said enzyme being preferably pancreatin, the hydrolysis step being carried on until the product contains no more residual proteins, i.e. is free of any nitrogen which can be precipitated by trichloracetic acid, 12%, then recovering the thus obtained hydrolyzate, which constitutes the total enzymatic hydrolyzate desired.

What we claim is:

1. A composition enriched in casein phosphopeptides comprising less than 4% of the aromatic amino acids phenylalanine, tyrosine and tryptophan; a serine amount of greater than 8% and less than 20%; and having a ratio of $Ca+Mg+P/N_T$ which is greater than 0.2, wherein $N_T$ is the total nitrogen content times 6.38; and a free amino acid content of less than 3%; said composition produced by a process consisting essentially of:
   (a) subjecting a casein-based material comprising phosphoscaseinates of a monovalent cation selected from the group consisting of sodium, potassium or ammonium; or paracasein derived from phosphoscaseinates of the same cations, to enzymatic hydrolysis by means of at least one proteolytic enzyme which is capable of substantially reproducing the proteic digestion which occurs in vivo in the human body to form a hydrolyzate containing peptides;
   (b) subjecting the hydrolyzate to at least one ultrafiltration step on a membrane which allows the peptides of the hydrolyzate to pass through in a permeate; said permeate containing phosphopetides and nonphosphorylated peptides;
   (c) adding to said permeate at least one bivalent cation-containing salt capable of forming aggregates of the phosphopeptides, thereby producing a mixture containing phosphopeptide aggregates and non-phosphorylated peptides; and
   (d) separating the phosphopeptide aggregates and non-phosphorylated peptides by subjecting the mixture to at least one ultrafiltration step with a membrane capable of retaining said phosphopeptide aggregates, and recovering said phosphopeptide aggregates to provide said composition.

2. The composition of claim 1, wherein said paracasein is obtained by:
   (a) treating a monovalent cation phosphocaseinate with rennet, to hydrolyze said phosphocaseinate;
   (b) precipitating the paracasein contained in the hydrolyzate to acidification to a pH of about 4.6; and
   (c) separating said precipitated paracasin.

3. The composition of claim 1, wherein the enzymatic hydrolysis is carried out in a device which combines an ultrafiltration apparatus with an ezymatic reactor.

4. The composition of claim 1, wherein said enzymatic hydrolysis is carried out continuously by feeding the casein-based material to a reaction zone source to cause intimate contact of the material with the proteolytic enzyme; continuously withdrawing reaction product from the reaction zone to an ultrafiltration zone, and continuously withdrawing from the ultrafiltration zone a permeate which comprises the hydrolyzate.

5. The composition of claim 1, wherein said enzymatic hydrolysis is carried out at a pH in the range of about 7 to 8.5.

6. The composition of claim 1, wherein said proteolytic enzyme is a pancreatin in the form of a natural pancreatic extract or a synthetic mixture of trypsin and α-chymotrypsin.

7. The composition of claim 1, wherein the enzymatic hydrolysis is carried out at a temperature in the range of 37°–45° C.

8. The composition of claim 7, wherein said enzymatic hydrolysis is carried out at a temperature in the range of 37°–40° C.

9. The composition of claim 8, wherein said enzymatic hydrolysis is carried out at a temperature of about 37° C.

10. The composition of claim 1, where in the phosphopeptides are in the form of calcium or magnesium salts of said phosphopeptides.

11. The composition of claim 1, wherein the phosphopeptides are in the form of oligoelement complexes of said phosphopeptides, wherein the oligoelements are selected from the group consisting of Fe, Zn, Cu, Cr, Ni, Co, Mn and Se.

* * * * *